(12) United States Patent
Miller et al.

(10) Patent No.: US 11,304,972 B2
(45) Date of Patent: *Apr. 19, 2022

(54) NITRIC OXIDE TOPICAL APPLICATION APPARATUS AND METHODS

(71) Applicant: SYK TECHNOLOGIES, LLC, Newport Beach, CA (US)

(72) Inventors: C. Michael Miller, Pleasant Grove, UT (US); Gordon K. Hill, Sandy, UT (US); A. John Pate, Provo, UT (US); David A. Bell, Farmington, UT (US)

(73) Assignee: Syk Technologies LLC, Provo, UT (US)

( * ) Notice: Subject to any disclaimer, the term of this patent is extended or adjusted under 35 U.S.C. 154(b) by 155 days.

This patent is subject to a terminal disclaimer.

(21) Appl. No.: 16/787,357

(22) Filed: Feb. 11, 2020

(65) Prior Publication Data

US 2020/0171079 A1    Jun. 4, 2020

Related U.S. Application Data

(60) Division of application No. 16/103,056, filed on Aug. 14, 2018, now Pat. No. 10,751,364, which is a
(Continued)

(51) Int. Cl.
| | |
|---|---|
| *A61K 33/00* | (2006.01) |
| *A61P 17/00* | (2006.01) |
| *A61K 9/00* | (2006.01) |
| *A61K 9/12* | (2006.01) |
| *A61K 31/19* | (2006.01) |

(Continued)

(52) U.S. Cl.
CPC ............ *A61K 33/00* (2013.01); *A61K 9/0014* (2013.01); *A61K 9/122* (2013.01); *A61K 31/19* (2013.01); *A61K 31/194* (2013.01); *A61K 31/375* (2013.01); *A61P 17/00* (2018.01); *A61K 47/12* (2013.01)

(58) Field of Classification Search
None
See application file for complete search history.

(56) References Cited

U.S. PATENT DOCUMENTS

| | | | |
|---|---|---|---|
| 3,682,171 | A | 8/1972 | Dali et al. |
| 5,045,292 | A | 9/1991 | Ruegg et al. |

(Continued)

FOREIGN PATENT DOCUMENTS

| | | |
|---|---|---|
| WO | WO 0220026 | 3/2002 |
| WO | WO 2008110872 | 9/2002 |

(Continued)

*Primary Examiner* — Aradhana Sasan
(74) *Attorney, Agent, or Firm* — Knobbe, Martens, Olson & Bear, LLP

(57) ABSTRACT

A topical application of nitric oxide may be provided by two separate containers, each containing an active component media to produce nitric oxide when combined. For example, a nitrite component media may be contained in one dispenser and an acidified component media may be contained in another dispenser. Each dispenser may dispense the respective component media as a foam. The resultant foams are combined to initiate the production of nitric oxide and the mixture of foams is applied topically to treat various skin disorders or wounds.

20 Claims, 1 Drawing Sheet

Related U.S. Application Data continuation of application No. 15/415,550, filed on Jan. 25, 2017, now Pat. No. 10,052,348.

(60) Provisional application No. 62/438,375, filed on Dec. 22, 2016, provisional application No. 62/432,744, filed on Dec. 12, 2016, provisional application No. 62/287,755, filed on Jan. 27, 2016.

(51) Int. Cl.
*A61K 31/194* (2006.01)
*A61K 31/375* (2006.01)
*A61K 47/12* (2006.01)

(56) References Cited

U.S. PATENT DOCUMENTS

| | | | |
|---|---|---|---|
| 5,047,166 A | 9/1991 | Weil | |
| 5,427,797 A | 6/1995 | Frostell et al. | |
| 5,713,349 A | 2/1998 | Keaney | |
| 5,823,180 A | 10/1998 | Zapol et al. | |
| 5,839,433 A | 11/1998 | Higgenbottam | |
| 5,869,539 A | 2/1999 | Garfield et al. | |
| 5,873,359 A | 2/1999 | Zapol et al. | |
| 5,891,472 A | 4/1999 | Russell | |
| 6,000,403 A | 12/1999 | Cantwell | |
| 6,019,100 A | 2/2000 | Alving et al. | |
| 6,063,407 A | 5/2000 | Zapol et al. | |
| 6,103,275 A | 8/2000 | Seitz et al. | |
| 6,131,572 A | 10/2000 | Heinonen | |
| 6,142,147 A | 11/2000 | Head et al. | |
| 6,149,606 A | 11/2000 | Alving et al. | |
| 6,432,077 B1 | 8/2002 | Stenzler | |
| 6,458,109 B1 | 10/2002 | Henley et al. | |
| 6,572,594 B2 | 6/2003 | Satterfield et al. | |
| 6,581,599 B1 | 6/2003 | Stenzler | |
| 6,601,580 B1 | 8/2003 | Bloch et al. | |
| 6,612,306 B1 | 9/2003 | Mault | |
| 6,670,323 B1 | 12/2003 | Looker et al. | |
| 6,749,834 B2 | 6/2004 | Fein et al. | |
| 6,763,832 B1 | 7/2004 | Kirsch et al. | |
| 6,786,217 B2 | 9/2004 | Stenzler | |
| 6,793,644 B2 | 9/2004 | Stenzler | |
| 7,017,573 B1 | 3/2006 | Rasor et al. | |
| 7,045,152 B2 | 5/2006 | Stamler | |
| 7,048,951 B1 | 5/2006 | Seitz et al. | |
| 7,066,356 B2 | 6/2006 | Schuman et al. | |
| 7,122,018 B2 | 10/2006 | Stenzler et al. | |
| 8,518,457 B2 | 8/2013 | Miller et al. | |
| 8,668,937 B2 | 3/2014 | Perricone et al. | |
| 8,685,467 B2 | 4/2014 | Miller et al. | |
| 8,720,436 B2 | 5/2014 | Jones | |
| 8,770,440 B2 | 7/2014 | Lin | |
| 8,980,331 B2 | 3/2015 | Chen et al. | |
| 9,730,956 B2 | 8/2017 | Stenzler et al. | |
| 10,052,348 B2 * | 8/2018 | Miller | A61K 9/0014 |
| 10,905,712 B2 | 2/2021 | Stenzler et al. | |
| 2002/0182162 A1 | 12/2002 | Shahinpoor et al. | |
| 2004/0002438 A1 | 1/2004 | Hawkins et al. | |
| 2005/0214193 A1 | 9/2005 | D'Ottone | |
| 2006/0172018 A1 | 8/2006 | Fine et al. | |
| 2007/0190184 A1 | 8/2007 | Montgomery et al. | |
| 2007/0239107 A1 | 10/2007 | Lundberg et al. | |
| 2008/0317679 A1 | 12/2008 | Tamarkin et al. | |
| 2010/0003349 A1 | 1/2010 | Miller et al. | |
| 2012/0048891 A1 | 3/2012 | Hagleitner | |
| 2013/0200109 A1 | 8/2013 | Yang et al. | |
| 2013/0330244 A1 | 12/2013 | Balaban et al. | |
| 2014/0296773 A1 | 10/2014 | Bulent et al. | |
| 2014/0335207 A1 | 11/2014 | Minton et al. | |

FOREIGN PATENT DOCUMENTS

| | | |
|---|---|---|
| WO | WO 2006110923 | 10/2006 |
| WO | WO 2007057763 | 5/2007 |
| WO | WO 2008116925 | 10/2008 |
| WO | WO 2013085784 | 6/2013 |
| WO | WO 2014031491 | 6/2013 |
| WO | WO 2013119642 | 8/2013 |

* cited by examiner

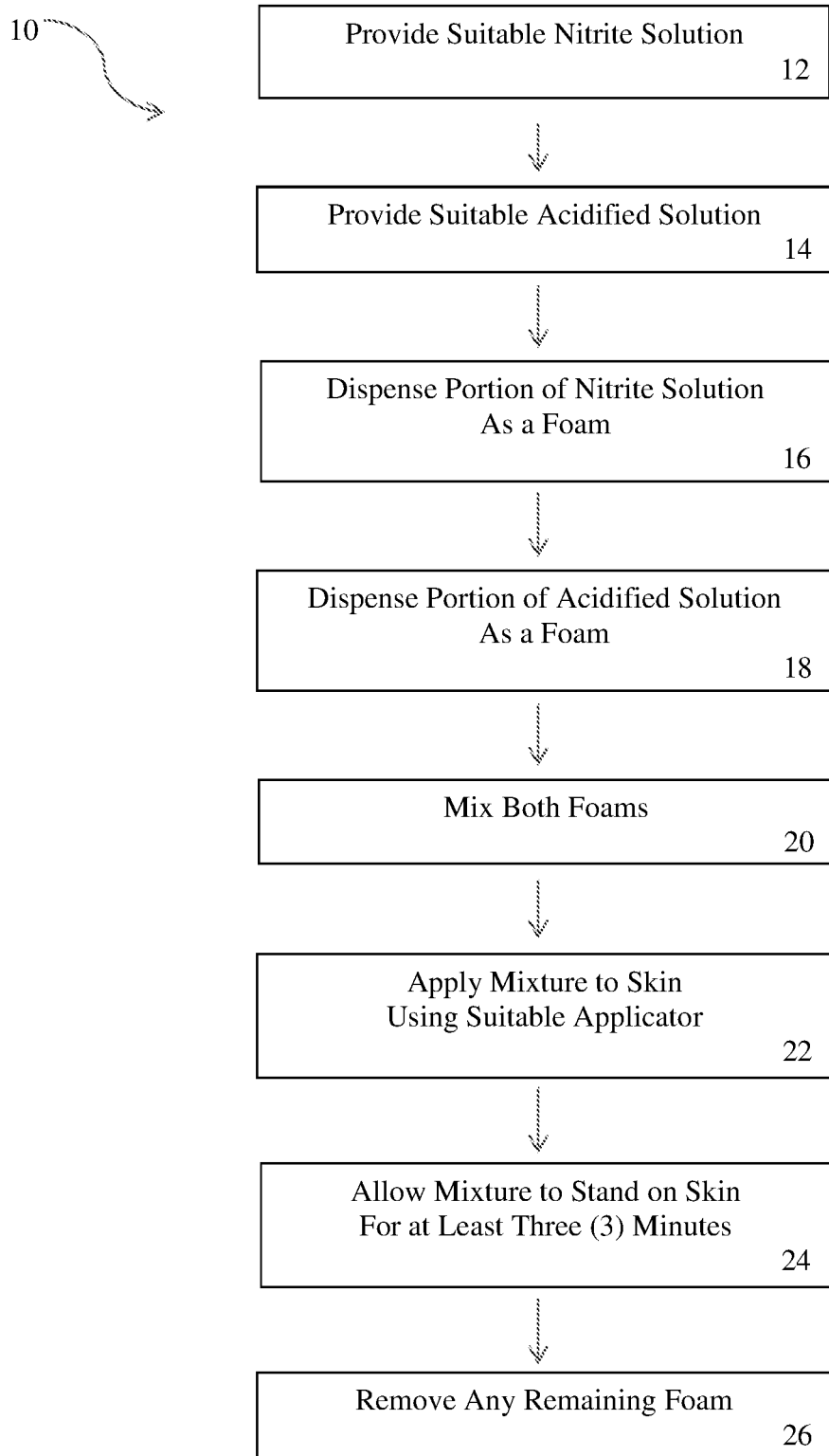

NITRIC OXIDE TOPICAL APPLICATION APPARATUS AND METHODS

RELATED APPLICATIONS

This application: is a divisional (continuation) of U.S. patent application Ser. No. 16/103,056, filed on Aug. 14, 2018; which is a divisional (continuation) of U.S. patent application Ser. No. 15/415,550 filed on Jan. 25, 2017, issued as U.S. Pat. No. 10,052,348 on Aug. 21, 2018; which claims the benefit of: U.S. Provisional Patent Application Ser. No. 62/287,755 filed on Jan. 27, 2016; U.S. Provisional Patent Application Ser. No. 62/432,744 filed on Dec. 12, 2016; and U.S. Provisional Patent Application Ser. No. 62/438,375 filed on Dec. 22, 2016; all of which are hereby incorporated by reference in their entireties.

BACKGROUND

1. The Field of the Invention

This invention relates to apparatus and methods for topical applications of nitric oxide media, and more specifically for transdermal absorption of nitric oxide through the use of nitric oxide producing reagents in foam or serum carriers.

2. Background

There are numerous benefits documented regarding the use of nitric oxide to help or treat humans having a variety of ailments, diseases, illnesses, or afflictions. The discovery of certain nitric oxide effects in live tissue garnered a Nobel Prize. Much of the work in determining the mechanisms for implementing, and the effects of, nitric oxide administration are reported in literature.

Various products have been developed and marketed that attempt to apply the known benefits of nitric oxide. Numerous patents and patent applications are available describing the benefits and uses of nitric oxide in various forms. For example: U.S. Pat. Nos. 5,891,472; 6,103,275; 8,668,937; 8,685,467; 8,720,436; Publication No. US20020182162 A1; Publication No. WO2008116925 A1; Publication No. US20130330244 A1; Publication No. WO2013085784 A1; and Publication No. US20140296773 A1, which are all incorporated herein by reference in their entireties as to all they teach.

Similarly, numerous patents and patent applications are available describing various methods of delivering nitric oxide. For example: U.S. Pat. No. 8,770,440; Publication No. US20120048891 A1; and Publication No. WO2013119642 A1, which are all incorporated herein by reference in their entireties as to all they teach.

Nitric oxide is considered an unstable molecule. This makes it difficult to develop a product that can consistently promote the formation of, or provide usable, nitric oxide to a person. What is needed is product and topical method of application that provides a comparatively efficient way to promote production of nitric oxide usable by human cells and tissues and available for treatment of various maladies.

BRIEF SUMMARY OF THE INVENTION

In accordance with the foregoing, certain embodiments of a product, compound and method in accordance with the invention provide a topical product that can be applied or used by a person to facilitate and promote the production of nitric oxide to be used by a person, especially with respect to the treatment of various maladies, illnesses, biofilms, injuries, or the like. The topical product may be suitably formulated to promote production of nitric oxide for use in human cells and tissues.

In one embodiment, the separate components of a product that provides a topical application system may be contained in separate containers. For example, a first solution may be contained in a first container and a second solution may be contained in a second container. Each container may then dispense the respective topical component in a foam, or foamy suspension. The resultant, foam, topical components may then be combined and applied to the skin surface of a person.

In one embodiment, a first solution may comprise water, sodium nitrite, and a cationic surfactant. A second solution may comprise water, lactic acid, citric acid, and the cationic surfactant. A portion of the first solution may be dispensed from the first container in a manner that produces a first foam. A portion of the second solution may be dispensed from the second container in a manner that produces a second foam. The first and second foams may be mixed to produce a resultant foam. Upon mixing of the first and second foams, nitric oxide begins to be produced. The resultant foam may be applied to a portion of skin intended to be treated. The resultant foam may be allowed to remain on the portion of skin for at least three (3) minutes, thereby allowing the resultant foam to collapse on the skin. The resultant foam may be allowed to remain on the portion of skin for a longer amount of time. After an appropriate period of time, any remaining resultant foam may be removed from the portion of skin.

A variety of skin disorders may be treated in such a manner, including without limitation, acne, cuts, scrapes, minor burns, ingrown hairs, etc.

Any suitable container may be used to contain the first and second solutions. In certain embodiments, a container that is capable of aerating and dispensing the solution as a foam may be used. For example, dispensers like those described in U.S. Patent Application US20130200109 and U.S. Pat. No. 7,066,356 may be utilized. Also, a dispenser like that sold under the tradename DIAL® Complete foaming antibacterial hand soap may also be utilized.

In one embodiment, a first solution may comprise approximately 100 mL of water, 10 g of sodium nitrite, and 1 g of the cationic surfactant. A second solution may comprise approximately 100 mL of water, 5 g of lactic acid, 6 g of citric acid, and 3 g of the cationic surfactant.

In one embodiment, a first solution may comprise approximately 100 mL of water, 10 g of sodium nitrite, 2 g of sodium bicarbonate, and 1 g of the cationic surfactant. A second solution may comprise approximately 100 mL of water, 5 g of lactic acid, 8 g of citric acid, and 3 g of the cationic surfactant.

In one embodiment, a first solution may comprise approximately 100 mL of water, 10 g of sodium nitrite, and 2 g of the cationic surfactant. A second solution may comprise approximately 100 mL of water, 5 g of lactic acid, 6 g of citric acid, and 6 g of the cationic surfactant.

In one embodiment, a first solution may comprise approximately 100 mL of water, 10 g of sodium nitrite, 2 g of sodium bicarbonate, and 1 g of the cationic surfactant. A second solution may comprise approximately 100 mL of water, 5 g of lactic acid, 8 g of citric acid, and 6 g of the cationic surfactant.

In at least one embodiment, the resultant foam mixture produces a nitric oxide to nitrogen dioxide ratio between approximately 90% and 120% during the time the resultant foam remains on the portion of skin. In at least one embodiment, the resultant foam produces a nitric oxide to nitrogen dioxide ratio averaging between approximately 60% and 70% during the time the resultant foam remains on the portion of skin. In at least one embodiment, the mixture produces a nitric oxide to nitrogen dioxide ratio averaging between approximately 60% and 80% from about 3 minutes after mixing to about 30 minutes after mixing.

In one embodiment, a first solution may comprise approximately 100 mL of water, 10 g of sodium nitrite, and 2 g of a cationic surfactant. A second solution may comprise approximately 100 mL of water, 5 g of lactic acid, 6 g of citric acid, and 6 g of the cationic surfactant. A mixture of a first portion of the first solution and a second portion of the second solution may be mixed, thereby producing nitric oxide upon the mixing of the first and second portions.

In multiple embodiments, the first solution may further comprise a salt buffer that regulates the reaction rate of nitric oxide production.

BRIEF DESCRIPTION OF THE DRAWINGS

The foregoing features of the present invention will become more fully apparent from the following description and appended claims, taken in conjunction with the accompanying drawings and experimental data. Understanding that these drawings and data depict only typical embodiments of the invention and are, therefore, not to be considered limiting of its scope, the invention will be described with additional specificity and detail through use of the accompanying drawings and data in which:

FIG. 1 illustrates a method for using nitric oxide as a topical treatment for skin disorders as described herein.

DETAILED DESCRIPTION OF THE PREFERRED EMBODIMENTS

It will be readily understood that the components of the present invention, as generally described herein, could be arranged and designed in a wide variety of different configurations or formulations. Thus, the following more detailed description of the embodiments of the system, product and method of the present invention, is not intended to limit the scope of the invention, as claimed, but is merely representative of various embodiments of the invention.

A person may obtain the benefits of nitric oxide therapy by utilizing a topical application that generates nitric oxide. The nitric oxide may affect the surface to which the topical application is applied, and may be absorbed by a surface such as skin, by transdermal absorption.

Two individual, separate, component media or solutions may be provided. The first medium is a nitrite medium and generally provides the nitrite reactants in some suitable form, such as sodium nitrite, potassium nitrite, or the like. The second medium is an acidified medium and generally provides at least one acidic reactant in some suitable form, such as citric acid, lactic acid, ascorbic acid, or the like.

Reaction rate and pH control may be achieved by using a mixture of multiple food-grade acids. Reaction rate may also be controlled or engineered by including an appropriate, sufficient amount of a salt buffer in one or both of the component media. For example, and not by way of limitation, the addition of sodium chloride (NaCl), or some other suitable salt compound, can be added to one or both of the component media. The sodium chloride may reduce the rate of reaction producing nitric oxide by interfering with the reduction of the nitrite compound. This type of salt buffer may be described as utilizing the salt compound to increase steric hindrance and thereby control, influence or engineer the rate of reaction.

When approximately equal amounts of the two individual components (media or solutions) are combined into a topical mixture, a reaction is initiated that produces nitric oxide.

Two containers may be provided, each container is capable of dispensing a suitable amount of a given medium (one of the two to be mixed). The containers may be identical in structure and composition, but need not necessarily be so. The containers may dispense the medium by a pump action, such as is common with lotions and soaps. The containers may dispense the medium by a squeezing or shaking action, such as is common with viscous or thixotropic shampoos, condiments, colloidal suspensions, gels, and other compositions. The containers may dispense the medium or solution by a pumping and aerating action, such as is common with soap solutions that are dispensed as foamy soaps.

The medium may be any suitable medium for containing and dispensing the reactants, for example, the medium or carrier may be a foam, gel, a serum, a solution, or a lotion.

A gel may be obtained by including a water-soluble polymer, such as methyl cellulose available as METHOCEL™, in a suitable solution. A serum may be obtained by including polyacrylate in a suitable solution. A foam may be obtained by placing a serum, or other suitable liquid, in an appropriate dispenser that may inject air into the serum or liquid and dispense the media as a foam. A lotion used to suspend the reactants for a nitrite lotion medium and an acidified lotion medium may be selected such as the JERGENS® brand hand and body lotion.

Generally, the media holding a matched pair of reactants should be essentially the same. The chemical characteristics of the media may not be strictly identical, but the physical compositions should be essentially the same so as to mix readily and not inhibit the reaction.

For example, a nitrite foam or gel medium may have a slightly acidic to neutral pH while an acidified foam or gel medium may have a more acidic pH than the corresponding nitrite foam or gel medium. Using a nitrite gel medium with an acidified lotion medium may not provide optimal results. Using different media may not provide the best rates for desired results, but would probably not be dangerous.

Generally, a topical application of nitric oxide may be provided by mixing equal amounts of a nitrite medium and an acidified medium. The mixture is then applied to the intended surface. The mixture may be applied to a person's skin, or even an open wound.

The mixture provides nitric oxide to the intended surface. As the nitrite medium is mixed with the acidified medium, the reduction of nitrite by the acid(s) leads to the release of nitric oxide. The exposure to nitric oxide may serve a variety of purposes.

A topical mixture that produces nitric oxide may be used for antimicrobial, antifungal, or similar cleaning purposes, including the breaking up or dispersing of a biofilm. Infectious diseases are caused by pathogens such as bacteria, viruses, and fungi. Antibacterial soaps can kill some bacteria, but not necessarily all bacteria. A topical mixture as described has been shown to kill as many as, and more, bacteria compared to commercially available antibacterial soaps or hospital-based instant hand antiseptics.

A topical mixture that produces nitric oxide may be used for localized analgesic purposes. The analgesic effect nitric oxide may be provided via topical application.

A topical mixture that produces nitric oxide may be used for anti-inflammatory purposes.

A topical mixture that produces nitric oxide may also be used to disperse a biofilm. Biofilms are colonies of dissimilar organisms that seem to join symbiotically to resist attack from antibiotics. Nitric oxide signals a biofilm to disperse so antibiotics can penetrate the biofilm. It is also believed that nitric oxide interferes with the uptake of iron.

A topical mixture that produces nitric oxide may be used to help heal various kinds of wounds. Tests have been performed wherein a topical mixture that produces nitric oxide as described herein is applied regularly to an open wound that is generally resistant to healing. The wound was seen to show significant healing within a few weeks.

For example, a person in Canada had poor circulation and unresponsive diabetic ulcers on the person's feet. The person was immobilized and in a wheel chair, and had been scheduled for amputation to remove the person's foot about a month after this experiment began. A topical mixture that produces nitric oxide was applied to the diabetic ulcers once a day. The person soaked the effected foot in a footbath solution that produces nitric oxide for approximately twenty minutes once every four days. Within two weeks the person was able to walk and go out in public. Within 4-6 weeks, the person was mobile and had achieved a substantially complete recovery. Meanwhile, the scheduled amputation was cancelled.

It was shown that a topical mixture that produces nitric oxide will kill squamous cells, pre-cancerous cells, if the concentration of nitric oxide is high enough. Tests intending to show that a topical mixture that produces nitric oxide would grow hair based in part on the increase of blood flow that accompanies application of nitric oxide actually showed that nitric oxide in as high doses provided as described herein above did kill squamous cells.

A topical mixture that produces nitric oxide may be used for more cosmetic purposes. The nitric oxide dose provided via topical application may reduce the appearance of wrinkles.

The nitrite medium may be formulated in any suitable medium and the concentration of reactants can be adjusted as desired as long as the intended reaction and sufficient concentrations of nitric oxide is obtained. For example, a suitable tank may be charged with distilled/deionized water (94.94% w/w) at room temperature (20°-25° C.). Sodium nitrite (3.00% w/w) and KATHON CG (0.05% w/w) may be dissolved in the water. METHOCEL™ (HPMC, cold dispersable; 1.75% w/w) may be stirred into the water until no lumps are present. Sodium hydroxide (10N to approximately pH 8; 0.09% w/w) may be rapidly stirred into the water to thicken, and care should be taken to avoid trapping air bubbles that can occur as a result of higher shear mixing.

EDTA, Na4 salt (0.10% w/w) may be stirred into the water until dissolved. Citric acid (crystalline; 0.08% w/w) may be added to adjust the mixture to a pH of 6.0. Small quantities of sodium hydroxide may be used to adjust the pH as needed. The individual percentages may be adjusted as desired for the best results.

The acidified medium may be formulated in any suitable carrier and the concentration of the reactants can be adjusted as desired as long as the intended reaction and sufficient concentrations of nitric oxide are obtained. For example, a suitable tank may be charged with distilled/deionized water (89.02% w/w) at room temperature (20°-25° C.). KATHON CG (0.05% w/w) may be dissolved in the water. METHOCEL™ (HPMC, cold dispersable; 1.75% w/w) may be stirred into the water until no lumps are present. Sodium hydroxide (10N to approximately pH 8; 0.09% w/w) may be rapidly stirred into the water to thicken, and care should be taken to avoid trapping air bubbles that can occur as a result of higher shear mixing.

EDTA, Na4 salt (0.10% w/w) may be stirred into the water until dissolved. Stirring may continue until the Methocel™ is completely hydrated. Lactic acid (85% liquid solution; 3.00% w/w) and ascorbic acid (USP, crystalline; 3.00% w/w) may be stirred in until completely dissolved. Citric acid (crystalline; 3.00% w/w) may be added to adjust the mixture to a pH of 6.0. Small quantities of sodium hydroxide may be used to adjust the pH as needed. The individual percentages may be adjusted as desired for the best results.

The use of at least two acids in producing the acidified medium may improve the shelf life of the acidified medium. Generally maintaining a pH of from about 3 to about 5 or above (so long as not too caustic for skin) has been found very useful in maintaining the shelf life of the product.

A topical mixture that produces nitric oxide has been shown to be effective in cleaning and disinfecting hands. For example, three sets of volunteers, with approximately 26 people in each set, participated in a test to determine the effectiveness of nitric oxide as a cleaning and disinfecting agent. The right and left hands of each person in each set of volunteers were swabbed with cotton-tipped applicators prior to any type of washing. The applicators were plated onto nutrient blood agar petri dishes using the three corner dilution method.

Each set of volunteers washed their hands using separate soaps for washing. The first set of volunteers washed their hands for thirty (30) seconds using a topical mixture of equal parts of nitrite gel medium and acidified gel medium as described herein above. The second set of volunteers washed their hands for thirty (30) seconds using a commercial anti-bacterial agent AVAGARD™D. The third set of volunteers washed their hands for fifteen (15) seconds using DIAL® Complete Foaming Hand Wash, and then rinsed for fifteen (15) seconds and dried.

The right and left hands of each person in each set of volunteers were swabbed again with cotton-tipped applicators after washing. The applicators were plated onto nutrient blood agar petri dishes using the three corner dilution method. All the blood agar petri dishes were incubated for forty-eight (48) hours at 35° C. The results were tabulated based on a grading scale of bacteria colonization. The testing showed that a topical mixture that produces nitric oxide reduced the relative bacterial content by approximately 62%. AVAGARD™D reduced the relative bacterial content by approximately 75%. DIAL® Complete Foaming Hand Wash reduced the relative bacterial content by approximately 33%. Thus, a topical mixture that produces nitric oxide was found to be approximately twice as effective and cleaning and disinfecting hands than DIAL® Complete Foaming Hand Wash and almost as effective as AVAGARD™D.

It has been determined that the dose required to kill bacteria on a surface, such as a person's skin, is at least approximately 320 ppm of nitric oxide. A topical gel mixture of approximately three (3) grams of nitrite gel medium and approximately three (3) grams of acidified gel medium that produces nitric oxide has been shown to deliver approximately 840 ppm of nitric oxide. Similarly, a topical gel mixture of approximately three (3) grams of nitrite lotion medium and approximately three (3) grams of acidified lotion medium that produces nitric oxide has been shown to deliver approximately 450 ppm of nitric oxide.

A variety of topical mixtures may be obtained by combining one of various types of nitrite mediums with one of various types of acidified mediums. For example and without limitation, a nitrite gel medium may be combined with an acidified serum medium, or vice versa. Likewise, other combinations of mediums are possible.

Different formulations may have different intended purposes. Ranges of acceptable constituents for each medium may include plus or minus 15% with any constituent.

In one embodiment, the component media, or just the active ingredients from each component media, may be added to a water bath so an area of skin may be allowed soak in the bath and absorb nitric oxide through the skin in this manner. The skin may be undamaged, or damaged or impaired in some way.

In one embodiment, one or more of the component media may include an effective amount of dimethyl sulfoxide (DMSO) to enable or promote additional absorption of nitric oxide through the skin.

In one embodiment, a dressing may be applied over the topical mixture of component media to enable or promote additional absorption of nitric oxide through the skin.

The use of a foam carrier may provide numerous benefits. The foam carrier may provide a sort of "dressing" or barrier that helps to promote the absorption of nitric oxide through the skin. The foam, and/or bubbles, may act as a barrier that keeps the nitric oxide gas produced as a result of the reaction nearer the skin. A bubble containing nitric oxide gas may burst near the skin allowing the nitric oxide to be absorbed transdermally. The foam may be placed on the skin and then allowed to collapse as opposed to being rubbed in. The foam carrier may provide a relatively easy process for metering each of the component media and thereby metering the amount of nitric oxide available. The foam carrier may also provide a method that uses less media as compared to other media.

Two individual, separate, component media may be provided. The first medium may be a nitrite medium and generally provides the nitrite reactants in some suitable form, such as sodium nitrite, potassium nitrite, or the like. The second medium is an acidified medium and generally provides at least one acidic reactant in some suitable form, such as citric acid, lactic acid, ascorbic acid, or the like. The first and second media may be provided in solution in a pump dispenser that produces a foam, or dispenser foam capable of aerating the solution and producing foam from the respective solutions.

In one embodiment, a suitable surfactant may be added to enable or promote the foaming of the respective component media. Generally, the surfactant may be a cationic surfactant that works in more acidic pH levels, and/or across a wider range of pH levels. A suitable surfactant may include Coco-Betaine, or Cocamidopropyl betaine.

The respective media may be used in conjunction with a mechanical foaming formulation.

In one embodiment, a first medium, or sodium nitrite solution, may be formulated to include 100 mL of water ($H_2O$), 10 g of sodium nitrite ($NaNO_2$), and 1 g of Coco Betaine.

In one embodiment, a second medium, or acid solution, may be formulated to include 100 mL of water ($H_2O$), 5 g of lactic acid ($CH_3CH(OH)CO_2H$), 6 g of citric acid ($C_6H_8O_7$), and 3 g of Coco Betaine.

In one embodiment, a first medium, or sodium nitrite solution, may be formulated to include 100 mL of water ($H_2O$), 10 g of sodium nitrite ($NaNO_2$), and 2 g of Coco Betaine.

In one embodiment, a second medium, or acid solution, may be formulated to include 100 mL of water ($H_2O$), 5 g of lactic acid ($CH_3CH(OH)CO_2H$), 6 g of citric acid ($C_6H_8O_7$), and 6 g of Coco Betaine.

The respective media may be used in conjunction with a chemical foaming formulation.

In one embodiment, a first medium, or sodium nitrite solution, may be formulated to include 100 mL of water ($H_2O$), 10 g of sodium nitrite ($NaNO_2$), 2 g of baking soda (sodium bicarbonate, $NaHCO_3$), and 1 g of Coco Betaine.

In one embodiment, a second medium, or acid solution, may be formulated to include 100 mL of water ($H_2O$), 5 g of lactic acid ($CH_3CH(OH)CO_2H$), 8 g of citric acid ($C_6H_8O_7$), and 3 g of Coco Betaine.

In one embodiment, a first medium, or sodium nitrite solution, may be formulated to include 100 mL of water ($H_2O$), 10 g of sodium nitrite ($NaNO_2$), 2 g of baking soda (sodium bicarbonate, $NaHCO_3$), and 2 g of Coco Betaine.

In one embodiment, a second medium, or acid solution, may be formulated to include 100 mL of water ($H_2O$), 5 g of lactic acid ($CH_3CH(OH)CO_2H$), 8 g of citric acid ($C_6H_8O_7$), and 6 g of Coco Betaine.

The amounts in the respective formulations may be adjusted by plus or minus 10%. Moreover, other ingredients may be added to any of the formulations for the respective media without disrupting or changing the efficacy of the media. For example, essential oils or other fragrances may be added to a first medium, a second medium, or both. Other components may include additives to increase surface tension and/or lower vapor pressure. For example, glycerol or glycerol-like components may be added in appropriate amounts. Other components or ingredients may be added depending on the desired effect on the respective media.

When approximately equal amounts of the two individual components (media) are combined into a topical mixture, a reaction is initiated that produces nitric oxide.

The respective media may be contained in two separate containers. Each container is capable of dispensing a suitable amount of a given medium (one of the two to be mixed). The containers may be identical in structure and composition, but need not necessarily be so. The containers may dispense the medium by a pump action and aerating the solution, thereby initiating or providing the foaming of the respective media.

The production and use of tighter, smaller bubbles in the foam carrier/media may help to produce less nitrogen dioxide ($NO_2$). The foam holds the nitric oxide (NO) closer to the skin, thereby allowing the nitric oxide to be absorbed transdermally while the nitrogen dioxide escapes because it is not as readily absorbed transdermally. It may be that tighter, smaller bubbles in the foam will help improve the nitric oxide therapy.

The size of the bubbles in the resultant foam may be influence by the type of foam dispenser used. The size of the bubbles in the resultant foam may also be influenced by appropriate components that are added to one or both of the solution media.

In one embodiment, a stronger acid may be used or included in a second medium, acid solution. For example, hydrochloric acid (HCl) may be used in a second medium, acid solution, to enable better production of nitric oxide.

Even the use of the salt buffer may provide additional benefits. The use of various cosmetic products from the Dead Sea is well-publicized. The use of a salt buffer enables the rate of the reaction producing nitric oxide to be controlled with or within less viscous media or carriers, like a solution or a foam carrier, as opposed to other processes that use increased viscosity or thixotropic media to control the rate of the reaction.

The use of additional cationic surfactant in foam media or foam carriers has been shown to produce less nitrogen dioxide ($NO_2$) when compared to other media, like gel media. This may be considered extremely beneficial since nitrogen dioxide is considered a pollutant and may cause irritation when inhaled.

Certain testing has been performed with respect to the production of nitric oxide and nitrogen dioxide using different types of media. Generally, a nitrite medium and an acidified medium may be mixed together in an enclosed container and the production of nitric oxide and nitrogen dioxide may be measured over time.

Example 1, a nitrite gel medium at a first concentration and an acidified gel medium at a first concentration are mixed together in an enclosed container and the production of nitric oxide and nitrogen dioxide measured. The production of nitric oxide averaged between approximately 20 ppm and 40 ppm over 60 minutes. The production of nitrogen dioxide averaged between approximately 60 ppm and 80 ppm over 60 minutes. After about 5 minutes, the ratio of nitric oxide to nitrogen dioxide was approximately 40.0% for up to 60 minutes. Put another way, mixing a nitrite gel and an acidified gel produced over twice as much nitrogen dioxide as compared to nitric oxide.

Example 2, a nitrite foam medium at a first concentration and an acidified foam medium at a first concentration are mixed together in an enclosed container and the production of nitric oxide and nitrogen dioxide measured. The production of nitric oxide averaged between approximately 20 ppm and 40 ppm over 60 minutes. The production of nitrogen dioxide averaged between approximately 20 ppm and 40 ppm over 60 minutes. After about 5 minutes, the ratio of nitric oxide to nitrogen dioxide was approximately 110.0% for up to 60 minutes. Put another way, mixing a nitrite foam and an acidified foam produced approximately equal amounts of nitric oxide and nitrogen dioxide.

Example 3, a nitrite gel medium at a second concentration, higher than the first concentration, and an acidified gel medium at a second concentration, higher than the first concentration, are mixed together in an enclosed container and the production of nitric oxide and nitrogen dioxide measured. The production of nitric oxide averaged between approximately 50 ppm and 100 ppm over 60 minutes. The production of nitrogen dioxide averaged between approximately 120 ppm and 80 ppm over 60 minutes. After about 5 minutes, the ratio of nitric oxide to nitrogen dioxide was between approximately 50.0% and 60.0% for up to 60 minutes. Put another way, mixing a more concentrated nitrite gel and a more concentrated acidified gel produced over twice as much nitrogen dioxide as compared to nitric oxide.

Example 4, a nitrite foam medium at a second concentration, higher than a first concentration, and an acidified foam medium at a second concentration, higher than a first concentration, are mixed together in an enclosed container and the production of nitric oxide and nitrogen dioxide measured. The production of nitric oxide averaged approximately 100 ppm over 60 minutes, with the production of nitric oxide almost continuously over 60 ppm and up to 150 ppm during that time. The production of nitrogen dioxide averaged between approximately 100 ppm and 60 ppm over 60 minutes, almost continuously over 60 ppm and up to 225 ppm during that time. After about 5 minutes, the ratio of nitric oxide to nitrogen dioxide was between approximately 60.0% and 100.0% for up to 60 minutes. Put another way, mixing a more concentrated nitrite foam and a more concentrated acidified foam produced slightly more nitrogen dioxide as compared to nitric oxide.

It has also been shown that an increased amount of cationic surfactant in the solutions produces more nitric oxide than nitrogen dioxide, especially in the initial stages of the reaction.

Example 5, a nitrite foam medium having a first concentration of cationic surfactant and an acidified foam medium having a first concentration of cationic surfactant are mixed together in an enclosed container and the production of nitric oxide and nitrogen dioxide measured. The production of nitric oxide for the first five (5) minutes averaged approximately 10 ppm. The production of nitric oxide for the next five (5) minutes averaged approximately 60 ppm. The production of nitrogen dioxide averaged between approximately 10 ppm and 0 ppm over the same ten (10) minutes.

Example 6, a nitrite foam medium having a second concentration of cationic surfactant, twice as much as the first concentration, and an acidified foam medium having a second concentration of cationic surfactant, twice as much as the first concentration, are mixed together in an enclosed container and the production of nitric oxide and nitrogen dioxide measured. The production of nitric oxide averaged between approximately 40 ppm and 70 ppm over the first ten (10) minutes. The production of nitrogen dioxide averaged between approximately 10 ppm and 0 ppm over the same ten (10) minutes.

Thus, the use of additional surfactant in the nitrite solution for producing a foam and the acidified solution for producing a foam did not hinder, or even aided, the production of nitric oxide, but also produced substantially lower levels of nitrogen dioxide produced.

It has been found that the levels of production of nitric oxide and nitrogen dioxide remain effectively consistent whether the foam is placed on a skin surface (i.e., the palm of the hand or the arm) or in a plastic tray.

As shown in FIG. 1, in one embodiment, a method 10 for topical, nitric oxide therapy may include the following steps: (1) provide a suitable nitrite solution 12; (2) provide a suitable acidified solution 14; (3) dispense a portion of the nitrite solution as a first foam 16 into a suitable container; (4) dispense a portion of the acidified solution as a second foam 18 into a suitable container; (5) mix the two foams together 20; (6) apply the mixed foam with a suitable applicator (i.e., a gauze pad or cotton swab) to an area of the skin intended for nitric oxide therapy 22; and (7) allow the mixed foam to remain on the skin for at least three (3) minutes (or between approximately three (3) to five (5) minutes and fifteen (15) minutes) 24. After the mixed foam has been allowed to stand on the skin and collapse or liquefy, any remainder may be wiped off 26. The mixed foam may be applied with a finger, or a finger from a gloved hand, but it has been found that applying the foam by using a cotton swab enables a better mechanical transfer of the foam to the intended skin area.

Other substantially similar methods of use may also provide similar benefits as those described.

It has been found that use of a nitric oxide producing foam provides beneficial results for a variety of skin disorders, including without limitation, acne, cuts, scrapes, burns, ingrown hairs, etc. Generally, a portion of a nitrite foam and a portion of an acidified foam are placed in a suitable container and mixed. The resultant, mixed foam is then placed on an area of skin intended for nitric oxide therapy. The resultant foam is allowed to remain on the skin for at least three (3) minutes, but generally not more than fifteen (15) minutes. This process is repeated twice a day.

Such a process was found to substantially clear an ingrown hair within approximately two weeks. This process was also found substantially promote healing of scrape wounds on skin that had remained open for approximately five (5) months, but were substantially healed after approximately two weeks of nitric oxide foam therapy. This process was also found to substantially clear zits that appeared near a hair line after a haircut within approximately ten (10) days. This process was also found to substantially promote healing of a new cut on a finger within approximately one week.

The present invention may be embodied in other specific forms and combinations without departing from its spirit or essential characteristics. The described embodiments are to be considered in all respects only as illustrative, and not restrictive. The scope of the invention is, therefore, indicated by the appended claims, rather than by the foregoing description. All changes which come within the meaning and range of equivalency of the claims are to be embraced within their scope.

What is claimed and desired to be secured by United States Letters Patent is:

1. A method for transdermal absorption of nitric oxide comprising:
    providing a first solution comprising water, at least one nitrite reactant, and a surfactant;
    providing a second solution comprising water, at least one acidic reactant, and the surfactant;
    dispensing a portion of the first solution;
    dispensing a portion of the second solution;
    mixing the portion of the first solution and the portion of the second solution to produce a resultant foam;
    applying the resultant foam to a portion of skin; and
    allowing the resultant foam to collapse.

2. The method of claim 1, further comprising:
    allowing the resultant foam to remain on the portion of skin for at least three minutes; and
    removing any remaining resultant foam from the portion of skin.

3. The method of claim 1, wherein:
    the first solution comprises approximately 100 mL of water, 10 g of sodium nitrite, and 1 g of the surfactant; and
    the second solution comprises approximately 100 mL of water, 5 g of lactic acid, 6 g of citric acid, and 3 g of the surfactant.

4. The method of claim 1, wherein:
    the first solution comprises approximately 100 mL of water, 10 g of sodium nitrite, 2 g of sodium bicarbonate, and 1 g of the surfactant, wherein the surfactant is a cationic surfactant; and
    the second solution comprises approximately 100 mL of water, 5 g of lactic acid, 8 g of citric acid, and 3 g of the surfactant, wherein the surfactant is a cationic surfactant.

5. The method of claim 1, wherein:
    the first solution comprises approximately 100 mL of water, 10 g of sodium nitrite, and 2 g of the surfactant; and
    the second solution comprises approximately 100 mL of water, 10 g of citric acid, and 6 g of the surfactant.

6. The method of claim 1, wherein:
    the first solution comprises approximately 100 mL of water, 10 g of sodium nitrite, 2 g of sodium bicarbonate, and 2 g of the surfactant; and
    the second solution comprises approximately 100 mL of water, 5 g of ascorbic acid, 8 g of citric acid, and 6 g of the surfactant.

7. The method of claim 3, further comprising:
    allowing the resultant foam to remain on the portion of skin for at least three minutes; and
    removing any remaining resultant foam from the portion of skin.

8. The method of claim 7, wherein the resultant foam produces a nitric oxide to nitrogen dioxide ratio averaging between approximately 90% and 120% during the time the resultant foam remains on the portion of skin.

9. The method of claim 6, further comprising:
    allowing the resultant foam to remain on the portion of skin for at least three minutes; and
    removing any remaining resultant foam from the portion of skin.

10. The method of claim 9, wherein the resultant foam produces a nitric oxide to nitrogen dioxide ratio averaging between approximately 60% and 70% during the time the resultant foam remains on the portion of skin.

11. A method for treating skin disorders comprising:
    providing a first solution comprising approximately 100 mL of water, 10 g of a nitrite reactant, and 2 g of a surfactant;
    providing a second solution comprising approximately 100 mL of water, 10 g of an acidic reactant, and 6 g of the surfactant;
    dispensing a portion of the first solution;
    dispensing a portion of the second solution;
    mixing the portion of the first solution and the portion of the second solution to produce a resultant foam;
    applying the resultant foam to a portion of skin to be treated; and
    allowing the resultant foam to remain on the portion of skin for at least three minutes, wherein the resultant foam produces a nitric oxide to nitrogen dioxide ratio averaging between approximately 60% and 70% during the time the resultant foam remains on the portion of skin.

12. The method of claim 11, wherein the nitrite reactant is selected from the group consisting of sodium nitrite and potassium nitrite; and the acidic reactant is selected from the group consisting of citric acid, lactic acid, salicylic acid, phosphoric acid, and ascorbic acid; and the surfactant is selected from the group consisting of coco-betaine and cocamidopropyl betaine.

13. The method of claim 11, wherein the first solution further comprises approximately 2 g of sodium bicarbonate.

14. The method of claim 11, wherein the first solution further comprises a salt buffer for regulating the reaction rate of nitric oxide production.

15. A method for topical application comprising:
    providing a first solution comprising approximately 100 mL of water, 10 g of a nitrite reactant, and 2 g of a surfactant;
    providing a second solution comprising approximately 100 mL of water, 10 g of an acidic reactant, and 6 g of the surfactant;
    dispensing a first portion of the first solution;
    dispensing a second portion of the second solution;
    mixing the first portion and the second portion to produce a resultant foam, wherein the mixing of the resultant foam initiates the production of nitric oxide;
    applying the resultant foam to a portion of skin; and
    allowing the resultant foam to collapse in response to contact with the portion of skin.

16. The method of claim 15, further comprising, allowing the resultant foam to remain on the portion of skin for at least three minutes.

17. The method of claim 16, wherein the resultant foam produces a nitric oxide to nitrogen dioxide ratio averaging between approximately 60% and 70% during the time the resultant foam remains on the portion of skin.

18. The method of claim 15, wherein the first solution further comprises approximately 2 g of sodium bicarbonate.

19. The method of claim 15, wherein the first solution further comprises a salt buffer for regulating the reaction rate of nitric oxide production.

20. The method of claim 15, wherein the nitrite reactant is selected from the group consisting of sodium nitrite and potassium nitrite; and the acidic reactant is comprised of at least two reactants selected from the group consisting of citric acid, lactic acid, salicylic acid, phosphoric acid, and ascorbic acid; and the surfactant is selected from the group consisting of coco-betaine and cocamidopropyl betaine.

* * * * *